(12) United States Patent
Rossi et al.

(10) Patent No.: US 7,087,031 B2
(45) Date of Patent: Aug. 8, 2006

(54) PERFECTED JOINTED ROD FOR A HIP SUPPORT

(75) Inventors: Paolo Rossi, Stansstad (CH); Aldo Bernareggi, Zoccorino (IT)

(73) Assignee: Orthoscharer & Co di Paolo Rossi & Co., Stansstad (CH)

( * ) Notice: Subject to any disclaimer, the term of this patent is extended or adjusted under 35 U.S.C. 154(b) by 543 days.

(21) Appl. No.: 10/302,311

(22) Filed: Nov. 22, 2002

(65) Prior Publication Data

US 2003/0100854 A1   May 29, 2003

(30) Foreign Application Priority Data

Nov. 27, 2001   (IT) .......................... MI2001A2492

(51) Int. Cl.
*A61F 5/00*   (2006.01)

(52) U.S. Cl. .......................................... 602/16; 602/19

(58) Field of Classification Search ................. 602/5, 602/16, 19, 20, 23; 128/882
See application file for complete search history.

(56) References Cited

U.S. PATENT DOCUMENTS

| | | | |
|---|---|---|---|
| 3,999,246 A * | 12/1976 | Suska .......................... 16/273 |
| 5,282,460 A | 2/1994 | Boldt | |
| 5,421,810 A * | 6/1995 | Davis et al. .................. 602/16 |
| 6,027,466 A * | 2/2000 | Diefenbacher et al. ....... 602/16 |
| 6,203,511 B1 * | 3/2001 | Johnson et al. ............... 602/16 |
| 6,254,559 B1 | 7/2001 | Tyrrell | |
| 6,494,853 B1 * | 12/2002 | Rossi et al. ................... 602/16 |

FOREIGN PATENT DOCUMENTS

EP   1 159 940   12/2001

OTHER PUBLICATIONS

EP Search Report.

* cited by examiner

*Primary Examiner*—Michael A. Brown
(74) *Attorney, Agent, or Firm*—James V. Costigan; Hedman & Costigan

(57) ABSTRACT

A perfected jointed rod for a hip support comprises at least one first element (15), suitable for being associated with a pelvis grip (12), and a second element (16), suitable for being associated with a thigh grip (13), reciprocally joined by at least one hinge (19) for a rotating movement in a first flexure-extension plane and by at least one articulated joint (20) for movement in a second abduction-adduction plane, wherein the articulated joint (20) is connected to an activating device which causes a movement of the second element (16) of the jointed rod (10) in the abduction-adduction plane with the rotation of said second element (16) with respect to the first element (15).

10 Claims, 4 Drawing Sheets

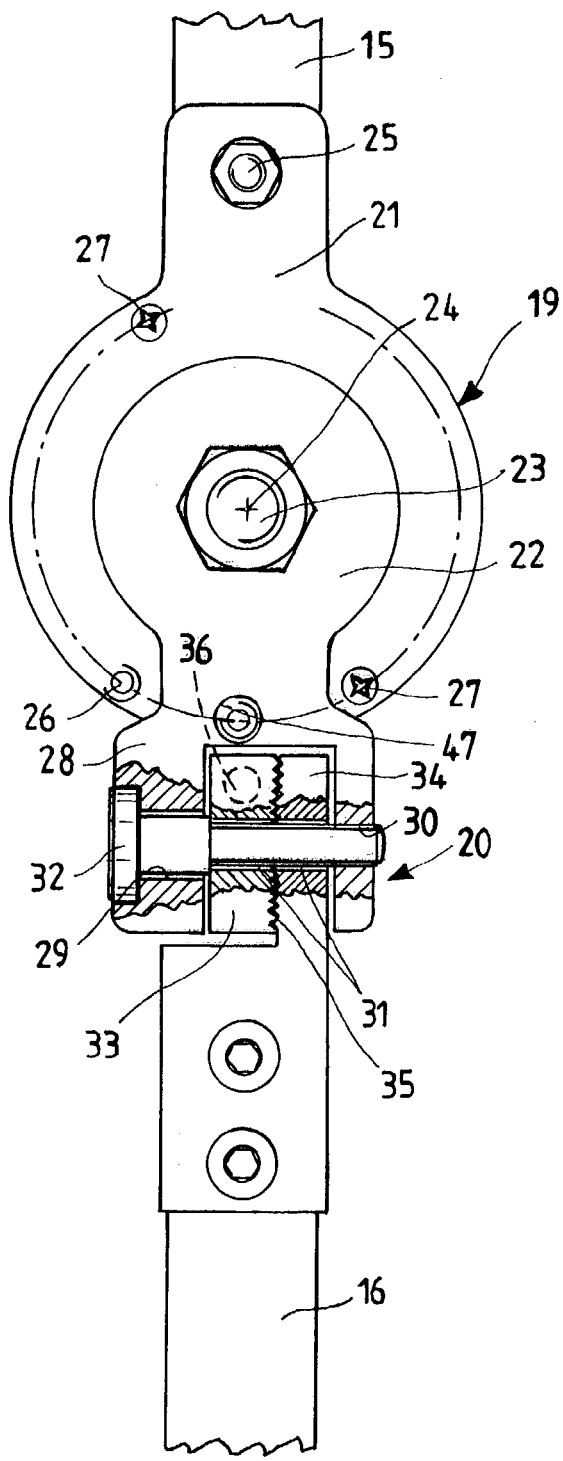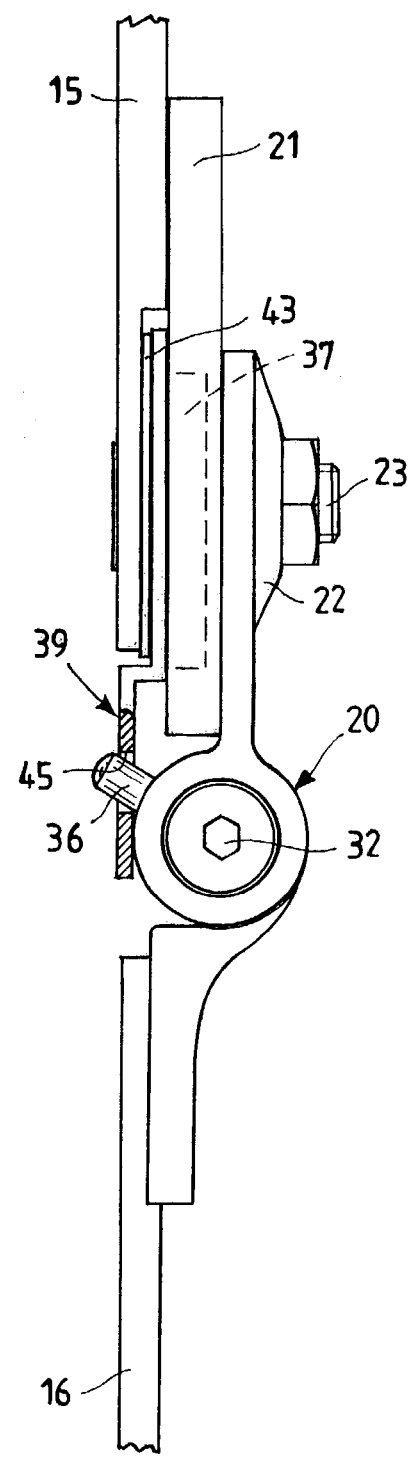

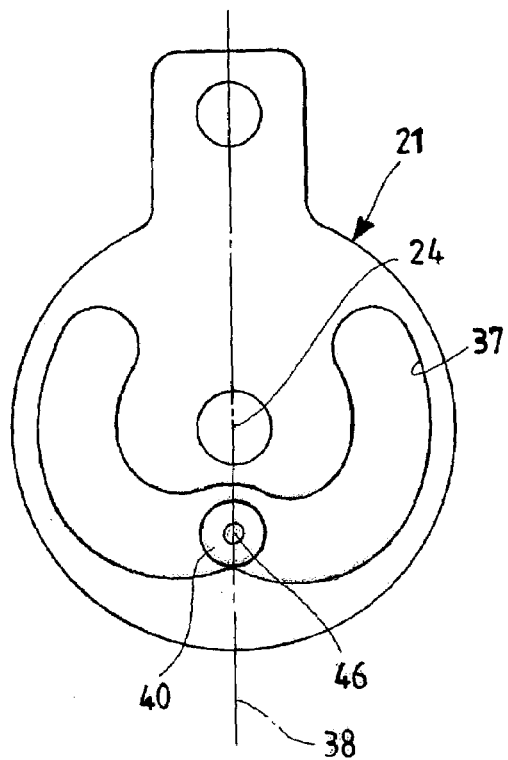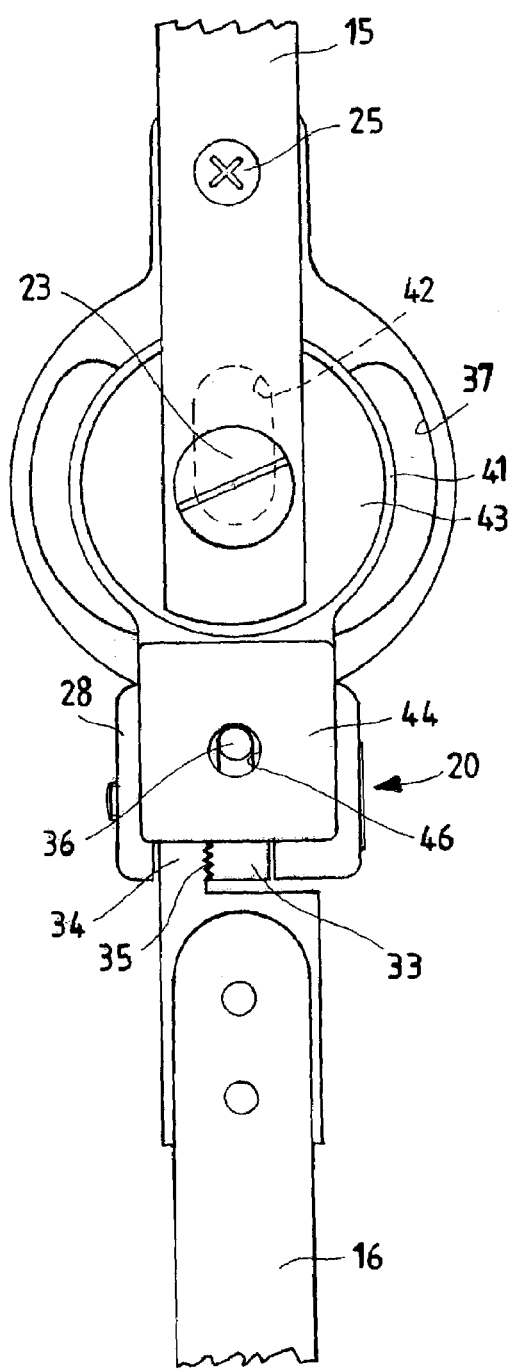

PERFECTED JOINTED ROD FOR A HIP SUPPORT

The present invention relates to a perfected jointed rod for a hip support.

Hip supports are medical devices prescribed, for example, for persons suffering from problems relating to chronic dislocation of the hip. In these patients, the head of the femur tends to easily slip out from the acetabulum, i.e. from its socket in the hip.

Dislocation of the hip is a pathology frequently occurring in patients with hip prostheses, consequently running the risk of having to re-undergo surgery.

Hip prostheses are applied to a large number of elderly people, mainly women, after fracturing their femur as a result of severe arthritis.

Patients with prostheses are not only vulnerable to dislocation of the hip but also have great difficulty in carrying out and controlling movement of the joints.

Hip supports have been available on the market for some time; they consist of a first element suitable for being applied to the pelvis, normally called "pelvis grip" connected by means of a jointed rod to a second element suitable for being applied to a thigh, called "thigh grip". The jointed rod limits the flexure-extension movement of the leg within an amplitude which is not dangerous for the patient.

Jointed rods generally consist of a first element to be connected to the pelvis grip and a second element to be connected to the thigh grip, hinged to each other.

European Patent EP 1068845 discloses the production of a hinged device consisting of two superimposed plates, joined in the rotation centre, each of which is attached to an element of the jointed rod. There are also elements for regulating the amplitude of the relative rotation between the plates, which can be suitably inserted in pre-fixed points for the purpose.

The rod described is also equipped with an articulated joint for regulating the abduction or adduction angle of the leg in relation to the physical conformation of each patient.

In spite of the use of hip supports, patients have great difficulty in movement, for example walking or passing from a sitting position to an upright position, or viceversa. In order to effect these movements, in fact, a healthy patient always tends to slightly rotate the thigh outwards. Following surgery, however, and the consequent inactivity during the rehabilitation period, patients, frequently elderly, lose their capacity to correctly control the abduction movement of the leg. This leads to a serious risk of falling and also greater stress on the prosthesized joint.

An objective of the present invention is to produce a perfected jointed rod for a hip support which helps the patient in controlling the abduction-adduction movement of the thigh during flexure-extension movement of the thigh itself.

Another objective of the present invention is to produce a jointed rod which can be rapidly and accurately regulated.

A further objective of the present invention is to produce a particularly simple and functional jointed rod, at limited costs.

These objectives according to the present invention are achieved by the production of a perfected jointed rod for a hip support as described in claim 1.

Further characteristics are specified in the dependent claims.

The characteristics and advantages of a perfected jointed rod for a hip support according to the present invention will appear more evident from the following illustrative but non-limiting description, referring to the schematic drawings enclosed, in which:

FIG. 2 is a plan view in a flexure-extension plane of a jointed portion in a straight position of a perfected rod for a hip support;

FIG. 3 is a side view in an abduction-adduction plane of the jointed portion of the rod of FIG. 2;

FIG. 4 is a plan view of the rear side of the jointed portion of the rod of FIG. 2;

FIG. 5 shows a detail of FIG. 4;

Figure 1:
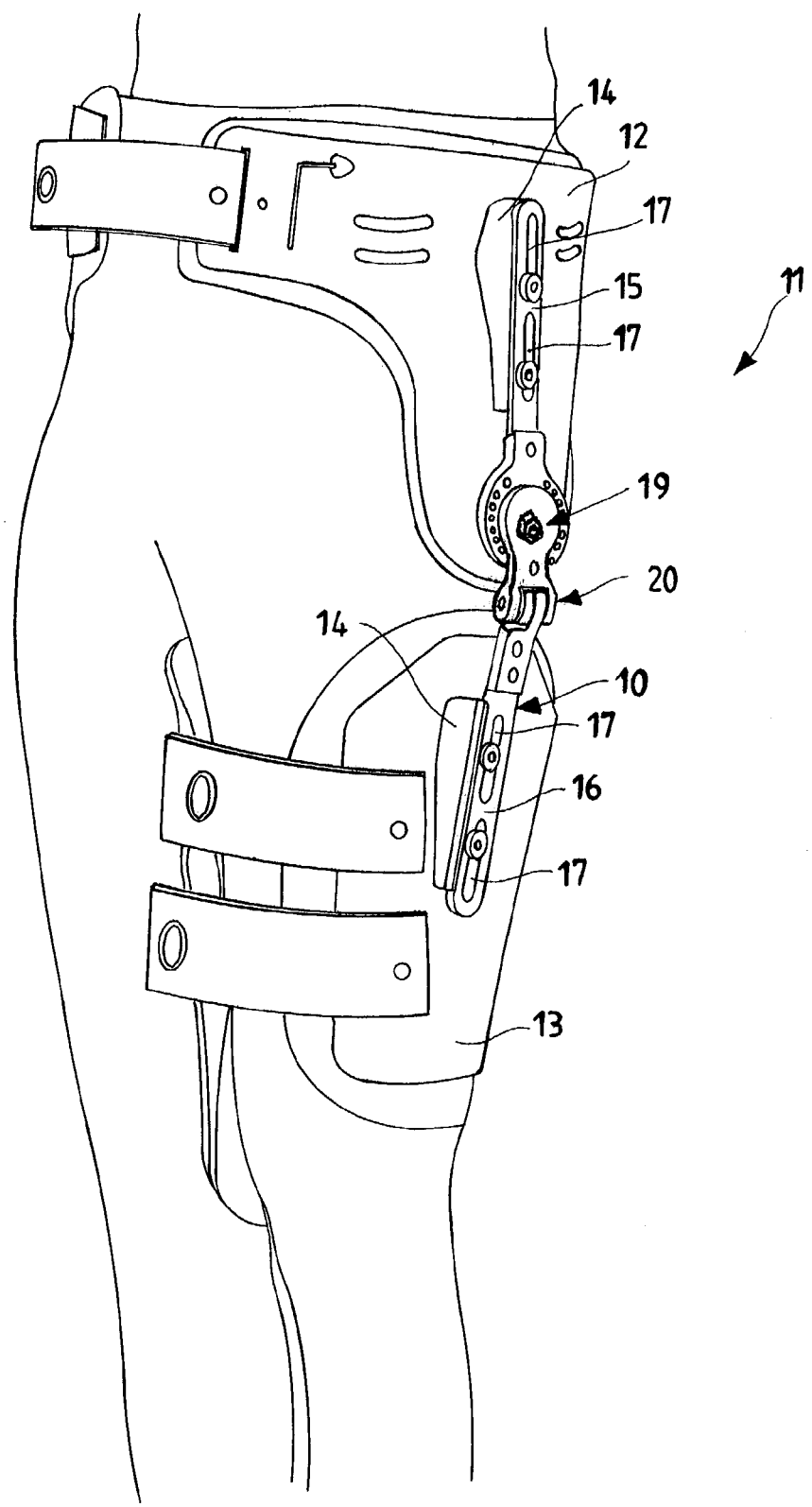
FIG. 1 shows a perfected jointed rod according to the invention assembled on a hip support.

With reference to the figures, these illustrate a perfected jointed rod 10 for a hip support, wherein the complete support is indicated as a whole with 11.

The support 11 comprises a pelvis grip 12 which is connected by means of the perfected jointed rod 10, object of the present invention, to a thigh grip 13.

The pelvis grip 12 and thigh grip 13 both have suitable seats 14 for respectively housing a first element 15 and a second element 16 of the jointed rod 10.

For example, FIG. 1 shows grooves or slots 17 for inserting screws 18 for fixing the rod 10 to the pelvis grip 12 and to the thigh grip 13 and for regulating the support 11 according to the height of the patient.

The first element 15 and the second element 16, which form the rod 10, are reciprocally joined by means of a jointed portion, illustrated in FIGS. 2 to 6, comprising a hinge 19 for a rotating movement in a first flexure-extension plane, and an articulated joint 20 for an angular regulation in a second abduction-adduction plane, which act in directions orthogonal to each other.

The hinge 19 shown in the figures is made up of two substantially disk-shaped plates, a base plate 21 and an upper plate 22. A threaded connection 23, of the screw-nut type, inserted in a through-hole, represents a rotation centre 24 of the hinge 19.

The base plate 21 is stably constrained, for example by means of a screw 25, to the first element of the rod 15; the upper plate 22 on the other hand is coupled by means of the articulated joint 20 with the second element 16.

Along the border of the base plate 21, there is a series of threaded holes 26 for positioning regulation elements 27, which limit the maximum rotational range of the upper plate 22 with respect to the base plate 21.

In a possible embodiment, not shown, a washer, preferably made of a self-lubricating plastic material, equipped, for example, with a graded scale for reading the rotation angle in the flexure-extension plane, is inserted between the plates 21 and 22.

At the lower end of the moveable upper plate 22, there is a bracket 28, whose ends are respectively equipped with a through-hole 29 and a threaded hole 30, arranged along the axis and in which a regulation element 32 of the articulated joint 20, for example a screw, is inserted.

The bracket 28 supports an entrainment disk 33 and also a disk-shaped end 34 of the second element 16, both equipped with a through-hole 31 for inserting the screw 32. Flat facing surfaces 35 of the disk 33 and end 34, orthogonally positioned with respect to that of the plates of the hinge 19, are equipped with teeth or other friction devices.

The disk 33 is also equipped with a piston pin 36, which radially extends outwards and forms an element of an activation device, which causes a movement of the second element 16 attached to the thigh grip 13 in the abduction-adduction plane with the rotation of said second element 16 with respect to the first element 15 of the rod 10.

FIGS. 4 and 5 reproduce the rear side of the jointed portion of the rod 10, object of the present invention. The base plate 21, illustrated in detail in FIG. 5, is equipped with cam devices, forming part of the activation device which guide the movement of an entraining element 39. A cavity 37, situated in the thickness of the base plate 21, is shaped with an omega profile and is symmetrical with respect to a median axis 38. The cavity 37 houses a cam follower 40, for example a roll or bearing, constrained to the entraining element 39 allowing it to rotate idle.

The element 39, which entrains the articulated joint 20, consists of one or more plates of varying thicknesses, comprising a portion 41 equipped with devices associated with the hinge 19 and a portion 44 equipped with devices associated with the articulated joint 20.

The circular portion 41 is equipped with a slot 42, indicated with dashed lines in FIG. 4, for connection with the base plate 21 and the first element 15 of the rod in the rotation centre 24 of the hinge 19. Said connection can possibly be effected by the interposition of a washer 43.

The circular portion 41 is equipped with devices, for example consisting of a pin, not shown, which is inserted with a certain clearance in a hole 46 of the bearing 40 housed in the cavity 37.

The portion 44 of the entraining element 39, is situated in correspondence with the articulated joint 20 and is equipped with a hole 45 in which the piston pin 36 of the entrainment disk 33 is inserted.

The perfected jointed rod, object of the present invention, consists in a preferred embodiment of a light structure made of aluminum alloy.

The cam devices, cavity 37 and cam follower 40 are exceptions, as they are made of steel or another low-wear material.

Furthermore, slipping parts are preferably made of or coated with an antifriction plastic material. The entraining element 39, in fact, can be made, for example, of a single piece, by covering the hole 45 with an antifriction plastic material. Alternatively it can be made up of several parts made of different materials joined to each other, wherein the portion 44, associated with the articulated joint 20, can advantageously consist of an antifriction plastic material.

The use and functioning of a perfected jointed rod 10 for a hip support according to the invention is substantially described below.

Following the instructions of the doctor, the regulation elements 27, against which the upper plate 22 is rested, is positioned by the technician so as to limit the movements of the leg to the desired degree. For example, in FIG. 2, the screws 27 are positioned so as to guarantee a rotation of about 120° of the rod 10 assembled on the left leg of the support 11, as illustrated in FIG. 1.

In order to obtain a jointed rod suitable for application to the right leg of the support, it is sufficient to position the regulation screws 27 in a specular way with respect to the plane by means of 38.

Should the orthopedic specialist feel that it is necessary to block the leg in an straight position, the screw 27 can be inserted into a hole 47 of the upper plate 22.

Once the support 11 has been fitted and the jointed rod 10 fixed to it, the technician regulates the articulated joint 20 adapting it to the physical conformation of the patient. By unscrewing the screw regulation element 32, the flat facing surfaces 35, equipped with teeth, of the disk 33 and end 34 of the second element 16, are released thus allowing the relative rotation.

Once the desired abduction angle to be applied to the extended leg, has been reached, the screw 32 is tightened and the entrainment disk 33 and end 34 of the second element 16 of the rod are blocked again.

Figure 6:
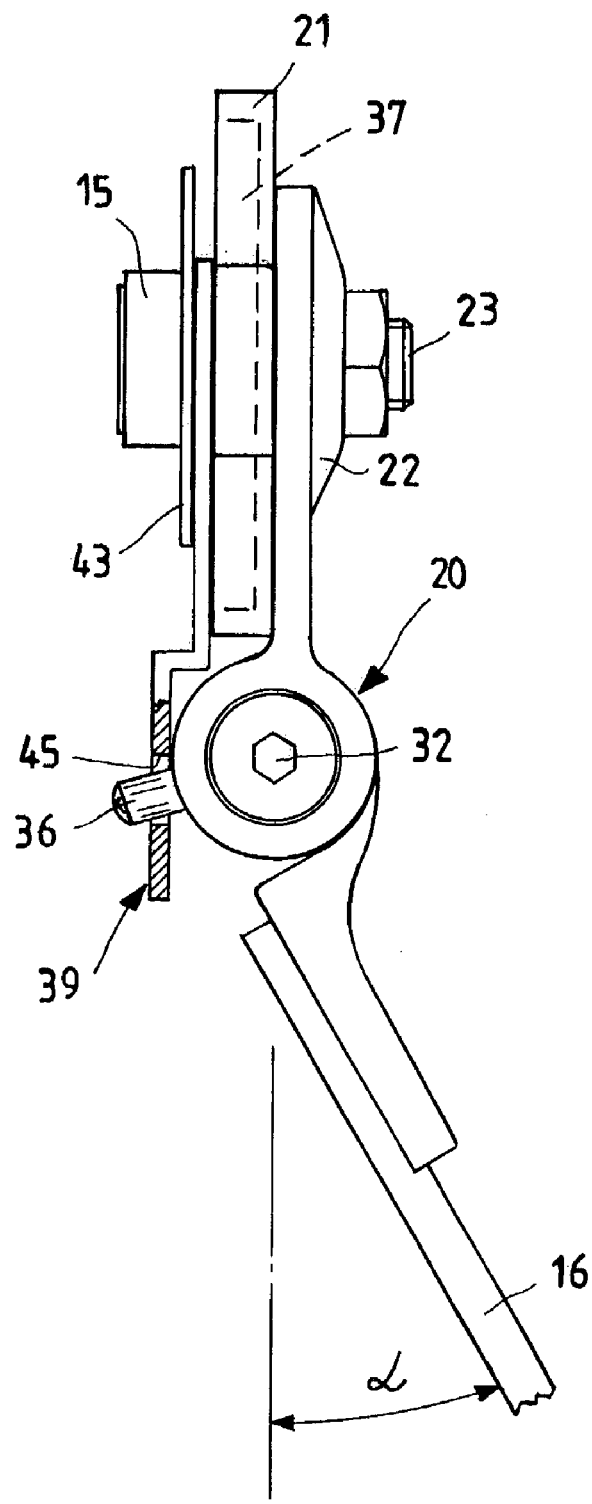
FIG. 6 is a side view of an abduction-adduction plane of the jointed portion of the perfected rod of FIG. 2, in which the elements of the rod are arranged in a position at an angle of 90°.

When the patient wearing the support moves the leg effecting a flexure-extension of the limb, i.e. passing from example from a position with the jointed rod 10 straight as in FIG. 3 to a position with the rod 10 at a right angle, schematized in FIG. 6, the perfected jointed rod, object of the present invention, imposes an additional forced abduction movement.

FIG. 6, in fact, schematizes the abduction angle a described in the second element 16 in the abduction-adduction plane contemporaneous with the flexure-extension movement.

More specifically, the flexure-extension movement of the limb, to which the second element of the rod 10 is attached by means of the support 11, causes the rotation of the upper plate 22 with respect to the base plate 21.

The entraining element 39 is forced to follow the rotation established by the piston pin 36 of the entrainment disk 33 inside the hole 45. The entraining element 39 carries with it the cam follower 40, or bearing, which however is compelled to follow the trajectory created by the shaped cavity with an omega profile 37. The bearing 40 is also idle with respect to the rotation around the pin itself.

The entraining element 39, which is constrained in the rotation centre 24 of the hinge 19 by means of the slot 42, progressively moves in a centrifugal direction, forcing the entrainment disk 33 to rotate as a result of the action of the piston pin 36. The second element 16 of the rod attached to the disk 33 by means of the toothed surfaces 35, consequently also progressively rotates by an abduction angle α.

The subsequent extension of the leg has an inverse effect, i.e. it causes the movement in a centripetal direction of the entraining element with a consequent progressive reduction in the abduction angle α.

In a second embodiment, not shown, the articulated joint can consist of the entrainment disk equipped with a piston pin, as described above, coupled with an extender stably constrained to an extension of the second element of the rod.

The perfected jointed rod for a hip support, object of the present invention, has the advantage of causing a gradual forced abduction-adduction movement contemporaneously with the flexure-extension of the limb. The jointed rod therefore helps patients with prostheses in their movements by simulating the correct functionality of the hip articulation.

Furthermore, the perfected jointed rod is advantageously simple to apply to the support and can be easily and accurately regulated. It is also suitable for persons with any physical structure, as the initial abduction angle can be regulated.

Numerous modifications and variations can be applied to the perfected jointed rod for a hip support thus conceived, all included in the scope of the invention; all the details, moreover, can be substituted by technically equivalent elements. In practice, the materials used, as also the dimensions, can vary according to the technical demands.

The invention claimed is:

1. A perfected jointed rod for a hip support comprising At least on first element (15), suitable for being associated with a pelvis grip (12), and a second element (16), suitable for being associated with a thigh grip (13), said first and second element (15 and 16) being reciprocally joined by at least one hinge (19) for a rotating movement in a first flexure-extension plane and by at least one articulated joint (20) for movement in a second abduction-adduction plane, wherein said articulated joint (20) is connected to an activating device which causes a movement of said second element (16) of the jointed rod (10) in said abduction-adduction plane with the rotation of said second element (16) with respect to the first element, wherein said activating device comprises an entraining element (39) equipped with means for the interaction with cam devices of said hinge (19) and with said articulated joint (20) and said cam devices consist of a cavity shaped with an omega profile (37) situated in the rear side of said base plate (21) and that said means associated with said hinge (19) consist of a cam follower (40) housed in said cavity (37).

2. The jointed rod according to claim 1, characterized in that said elements associated with said articulated joint (20) consist of a piston pin (36) which extends radially from said entrainment disk (33) and is inserted in a hole (45) of said entraining element (39).

3. The jointed rod according to claim 1, wherein said entraining element (39) is equipped with a slot (42) for connection in a rotation centre (24) of said hinge (18).

4. The jointed rod according to claim 1, wherein said articulated joint (20) is supported by a bracket (28).

5. The jointed rod according to claim 1, wherein said articulated joint (20) comprises an entrainment disk (33) and an end (34) of said second element (16) of said rod (10) joined by means of regulation elements (32).

6. The jointed rod according to claim 5, wherein said articulated joint (20) is equipped with flat facing surfaces (35) having friction devices.

7. The jointed rod according to claim 1, wherein said hinge (19) and said articulated joint (20) act on planes orthogonal to each other.

8. The jointed rod according to claim 1, wherein said cavity (37) and said cam follower (40) are made of steel.

9. The jointed rod according to claim 1, wherein said hole (45) is coated with an antifriction plastic material.

10. The jointed rod according to claim 1, wherein said entrainment element (39) consists of several parts, wherein one portion (44) containing said hole (45) is made of an antifriction plastic material.

* * * * *